United States Patent
Suh et al.

(10) Patent No.: US 7,494,686 B2
(45) Date of Patent: Feb. 24, 2009

(54) METHOD OF PRODUCING A PATCH TAPE SHOWING STRIPES OF ANISOTROPIC MAGNETIC FIELD

(76) Inventors: Jung Suk Suh, 126-2, 5 Ave, Ulziro, Jung-Gu, Seoul (KR); Kelly Lucas, Regan Building, Suit #5, 3161 E. Palmer Wasilla-Hwy, Wasilla, AK (US) 99654; Yong Ki Chong, 10700 174th St. S.E., Suit #106, Renton, WA (US) 98055

( * ) Notice: Subject to any disclaimer, the term of this patent is extended or adjusted under 35 U.S.C. 154(b) by 632 days.

(21) Appl. No.: 11/294,206

(22) Filed: Dec. 6, 2005

(65) Prior Publication Data

US 2007/0128348 A1 Jun. 7, 2007

(51) Int. Cl.
*A61L 33/00* (2006.01)

(52) U.S. Cl. ............ 427/2.1; 600/15; 427/128; 427/131; 427/202; 427/359; 427/407.1; 427/428.01

(58) Field of Classification Search .......... 128/76; 428/403; 600/15; 427/2.1

See application file for complete search history.

(56) References Cited

U.S. PATENT DOCUMENTS

| 4,539,261 | A | * | 9/1985 | Nakata et al. ............ 428/403 |
| 5,022,389 | A | * | 6/1991 | Brennan ............... 606/204.45 |
| 6,217,505 | B1 | * | 4/2001 | Sakuma ................... 600/15 |
| 6,344,021 | B1 | * | 2/2002 | Juster et al. ............... 600/15 |

* cited by examiner

*Primary Examiner*—Michael Barr
*Assistant Examiner*—Andrew Bowman (57) ABSTRACT

A method for manufacturing a magnet patch tape to facilitate blood circulation in a restricted area of a human body is provided. The patch tape shows a number of stripes of anisotropic magnet field with 2 to 5 mm width and spaced 1 to 3 mm apart from each other when viewed through a magnetic field viewer. The procedure of manufacturing the patch tape is comprised of the following steps: 1) prepare a slurry of anisotropic magnetic powder with surfactant, 2) coat a roll of plastic basic film with protecting layer via coating rollers, 3) paste adhesive to the coated film, 4) paste slurry of anisotropic magnetic powder on the proceeding coated film via a roller, 5) evaporate the surfactant, 6) coat the anisotropic magnet powder on the pasted surface of the film with adhesives, 7) stabilize the adhesives by passing through a ridge roller to form a patch tape, 8) stretch the patch tape with a draw down winder, 9) expose the magnet patch tape to a magnetizer to develop anisotropic magnetic field stripes, and 10) cut the tape into a desired size.

1 Claim, 10 Drawing Sheets

METHOD OF PRODUCING A PATCH TAPE SHOWING STRIPES OF ANISOTROPIC MAGNETIC FIELD

FIELD OF THE INVENTION

Current application is related with a method of producing an anisotropic magnetic patch tape, especially a magnetic patch tape having stripes of anisotropic magnetic field of 2 to 5 mm wide and spaced 1 to 3 mm apart from each other.

BACKGROUND OF THE INVENTION

Influence of magnetic field to human blood circulation is not widely known to the public. But, it is known that human blood is composed of liquid called plasma, which contains suspended cells of red blood cells, white blood cells, and platelets. Plasma, 90% is water, typically accounts for 55% by volume of blood and of the left 45% is from the red blood cells that make up 99% of the cells in the blood. The red blood cells are the principal carriers of the red colored hemoglobin molecules, an iron containing protein and binds about 97% of all oxygen in the body. Dr. Kenneth R. Bridges, M.D., Associate Professor of Medicine at Harvard Medical School, reported that the red blood cells change the shape from biconcave shape to a sickle shape when oxygen is deficient. The normal red cells retain their biconcave shape and move through the smallest capillaries without problems. But, the hemoglobin polymerizes in sickle red cells when they release oxygen and deforms the red cells. The membranes of the red blood cells become rigid in part due to repeated episodes of hemoglobin polymerization/depolymerization as the cells pick up and release oxygen in the circulation. These rigid red blood cells fail to move through the small blood vessels, blocking local blood flow to a micro-scopic region of tissue. Meanwhile, James D. Livingston, Professor of the Department of Materials Science and Engineering at the Massachusetts Institute of Technology, reported the influence of the magnetic field to human body in terms of increasing blood circulation in Skeptical Inquirer 25-30, 58, 1998. According to Professor Livingston, the human body, like its primary constituent, water, is diamagnetic. In response to an applied magnetic field, the electrons in water molecules make slight adjustments in their motions, producing a net magnetic field in the opposing direction about 100,000 times smaller than the applied field. Some literature suggests that magnetic fields attract blood, citing all the iron it contains. But, the net effect of the weak paramagnetism of the isolated iron atoms in hemoglobin is only a slight decrease in the overall diamagnetism of blood. Blood, like water, is weakly repelled by magnetic fields, not attracted. The results of the Baylor study raise the possibility that at least in some cases, topical application of permanent magnets may indeed be useful in pain relief, a conclusion that should be regarded as tentative until supported by further studies. Any mechanism for such an effect remains mysterious, but an effect of static magnetic fields on the complex electrochemical processes of the human body is not impossible. The inventor of the current application developed a magnet patch based on an assumption that the polymerized red blood cells align in a row under the influence of magnetic field and move through the smallest capillaries without problems. It is the purpose of the current application to provide a method of producing magnet patches that is effective for facilitating blood circulation.

DESCRIPTION OF THE PRIOR ARTS

U. S. Pat. RE38,042, RE38,042, RE38,042, U.S. Pat. Nos. 5,096,509, and 4,983,232 to Endoh, et al. illustrate magnetically anisotropic magnetic powder having an average particle size of 1-1000 µm made from a magnetically anisotropic R-TM-B—Ga or R-TM-B—Ga-M alloy having an average crystal grain size of 0.01-0.5 µm.

U. S. Pat. Nos. 5,085,715, 4,952,239, and 4,921,553 to Tokunaga, et al. illustrate a process for producing magnetically anisotropic powder having "flattened" crystal grains of an R-TM-B-M system alloy with preferably (c)/(a) greater than 2, where (c) is the grain size perpendicular to the C-axis and (a) the grain size parallel to the C-axis, includes the steps of plastically deforming a green compact of flakes formed by rapidly-quenching the alloy melt, and then crushing the plastically deformed body.

U. S. Pat. No. 4,842,656 to Maines, et al. illustrates a magnetically anisotropic powder having high coercivity and containing the magnetic phase $Nd_2Fe_{14}B$ is produced by melt spinning a composition of these elements to form amorphous or extremely finely crystalline particles which are hot worked to produce grains containing the above phase and having dimensions in the range of about 20 to 500 nanometers.

U. S. Pat. No. 4,745,001 to Miyoshi, et al. illustrates a process for preparation of a magnetic recording medium. It comprises the steps of applying a magnetic paint onto a surface of a nonmagnetic support to form a coated paint layer, said magnetic paint comprising magnetic recording layer-forming components including a ferromagnetic powder, an abrasive and a resin component dispersed in an organic solvent, and then subjecting the coated layer to magnetic orientation.

U.S. Patent Application 20040004523 to Humphries, David E., et al. discloses a hybrid magnetic structure made from a combination of anisotropic magnets and ferromagnetic pole materials, which are assembled in a predetermined array. The hybrid magnetic structure contains blocks of anisotropic magnets aligned in rows between ferromagnetic bars. The permanent magnet material is assembled with the magnetization orientation orthogonal to a lateral plane of the ferromagnetic poles and in opposing directions, to create a large pole-to-pole scalar potential difference that results in high magnetic flux density between the upper pole tips and a corresponding, alternating polarity.

U. S. Pat. No. 5,034,754 to Taylor, et al. illustrates a device for visually displaying magnetic patterns recorded on a planar medium. It is comprised of a transparent plate and a polyvinyl chloride membrane of 35 µm thick secured to the underside of the plate with 0.5 mm clearance between them. The clearance is filled with an aqueous solution of suspending detergent and carbonyl iron powder. When the plate is placed in juxtaposition with the planar medium the particles agglomerate to assume positions in conformity with the magnetic patterns.

None of the prior art illustrate a method of developing stripes of anisotropic magnetic field of 2 to 5 mm wide aligned in rows as shown in the current application.

SUMMARY OF THE INVENTION

The inventor of the current application developed a magnet patch based on an assumption that the polymerized red blood cells align in a row under the influence of magnetic field and move through the smallest capillaries without problems and releases pain. A method for producing a magnet patch tape to facilitate blood circulations in a restricted area of a human body is provided. The patch tape shows a number of stripes of anisotropic magnet field with 2 to 5 mm width and spaced 1 to 3 mm apart from each other when viewed through a magnetic field viewer. The procedure of manufacturing the patch tape is comprised of the following steps: 1) prepare a slurry of anisotropic magnet powder by adding a small amount of surfactant solution to the powders of anisotropic magnet to prevent aggregation of the magnetic powders, 2) coat a roll of plastic basic film with protecting layer of LDPE (Low Density Polyethylene) via coating rollers, 3) paste adhesive to the coated film, 4) paste slurry of anisotropic magnetic powder on the proceeding coated film via a roller, 5) evaporate the surfactant via a drier, 6) coat the anisotropic magnet powder pasted surface of the film with adhesives, 7) stabilize the adhesives by passing through a ridge roller to form a patch tape, 8) stretch the patch tape with a draw down winder, 9) expose the magnet patch tape to a magnetizer to develop anisotropic magnetic field stripes, and 10) cut the tape into a desired size. Clinical test on patients of muscle pain and Rheumatism reported release of pain. Patching the tape on the skin of an abscess for 24 hours removes the abscess.

DETAILED DESCRIPTION OF THE PREFERRED EMBODIMENT

Figure 1:
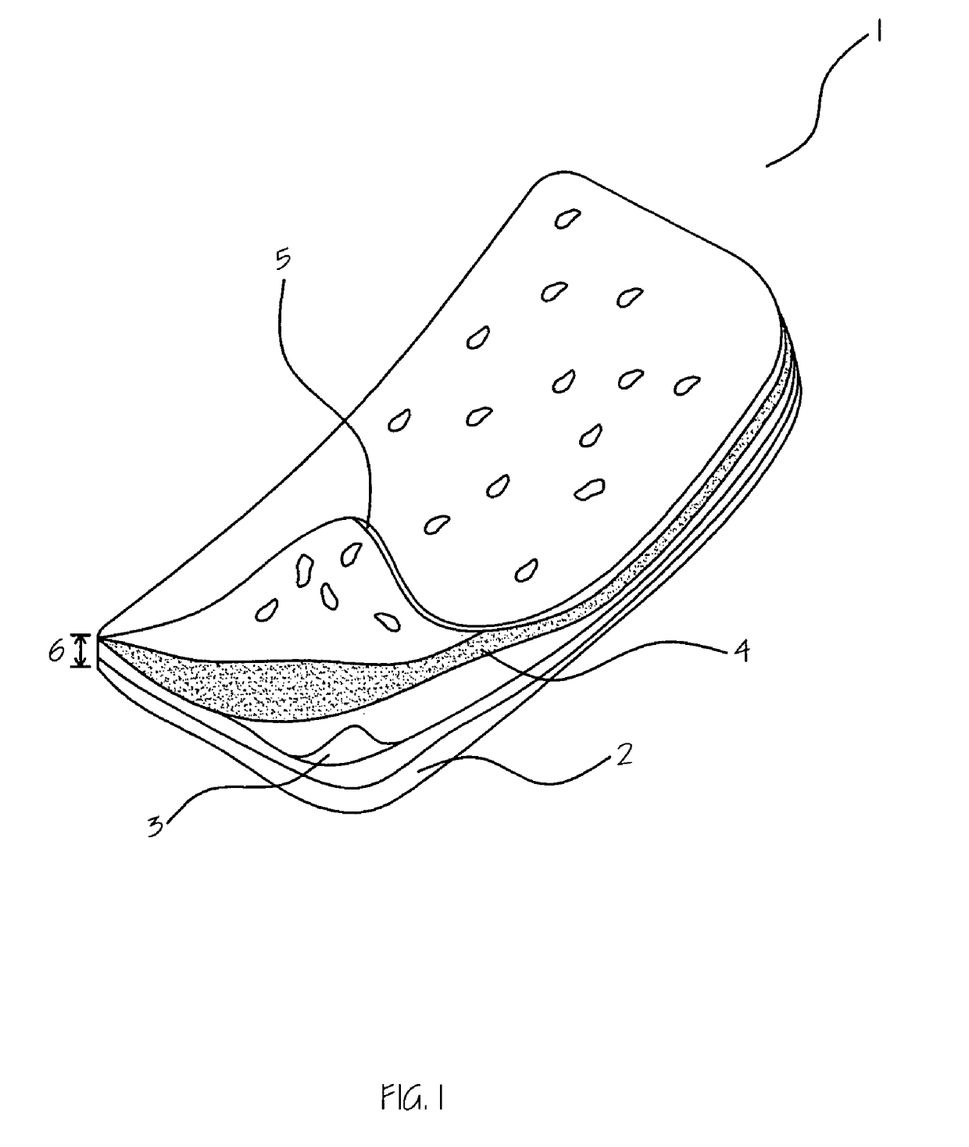
FIG. 1 is a schematic drawing of the anisotropic magnetic field maintaining patch tape of the current application.

FIG. 1 is a schematic drawing of the anisotropic magnet field maintaining patch tape (magnetic patch tape) (1) of the current application. The magnetic patch tape (1) is comprised of a basic texture (2) maintaining the overall shape of the patch tape, a coating layer (3), an LDPE (Low density Polyethylene) film, to prevent a first adhesive, epoxy monomers, from smearing into the texture (2), a mixed layer (4) of epoxy resin and anisotropic magnetic powders, and a second adhesive layer (5) of polyols that is to adhere to a user's skin. Total thickness of the magnetic patch tape is 0.2 to 0.3 mm and fabricated in various size and shapes, such as squares, circles and stars.

Figure 2:
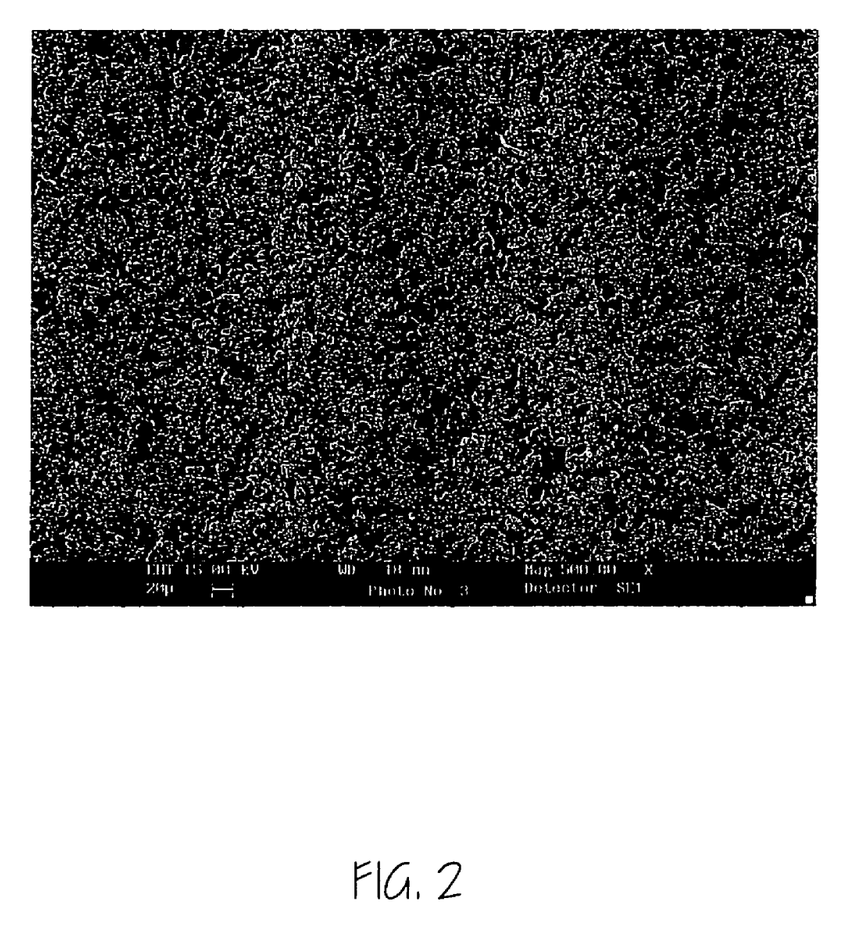
FIG. 2 is a Scanning Electron Microscopy of the surface of the magnet patch tape without second adhesive layer, showing the anisotropic magnet powders immobilized on Epoxy. Order of magnitude is 500.

FIG. 2 is a Scanning Electron Microscopy of the surface of the magnet patch tape (1), without the second adhesive layer, showing the anisotropic magnet powders immobilized on Epoxy adhesive. Order of magnitude is 500 times. Aggregates of magnetic powders and Epoxy adhesives are distributed evenly throughout the surface. Average particle size of anisotropic magnet particles used for current application is less than 1 μm.

Figure 3:
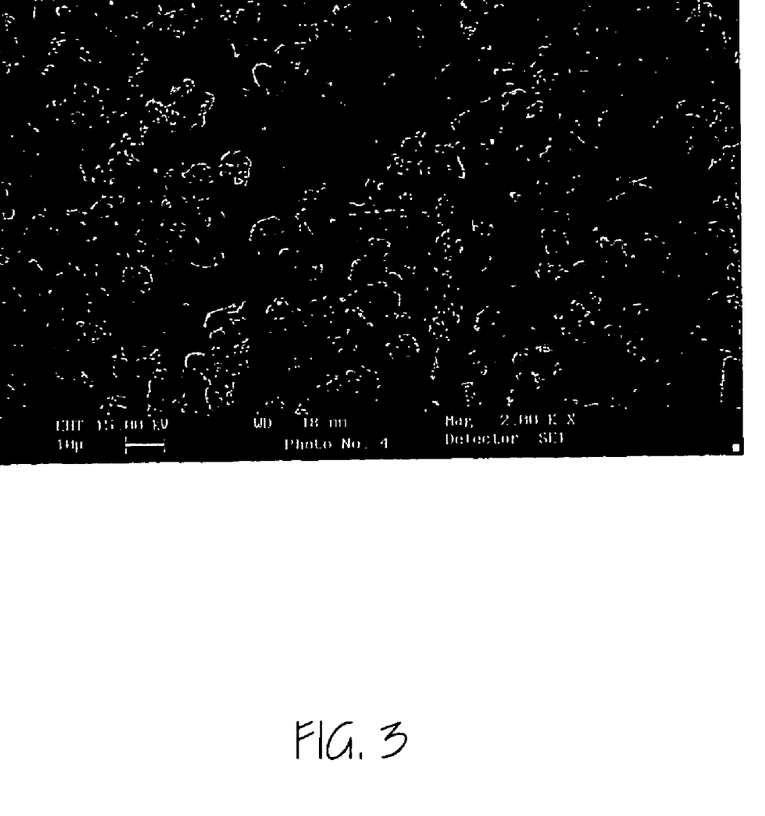
FIG. 3 is a Scanning Electron Microscopy of the surface of the magnet patch tape without second adhesive layer, showing the anisotropic magnet powders immobilized on Epoxy. Order of magnitude is 2,000.

FIG. 3 is a Scanning Electron Microscopy of the surface of the magnet patch tape without the second adhesive layer, showing the anisotropic magnet powders immobilized on Epoxy adhesive. Order of magnitude is 2,000 times. Small particles of few μm size (small light colored particles having sharp shape) are aggregated on the Epoxy backbone structure. The voids are formed by solvents of the Epoxy monomer mixture and other volatile slurrifying medium, Vertrel XF from DuPont, which is used in slurrifying the anisotropic magnet powders.

Figure 4:
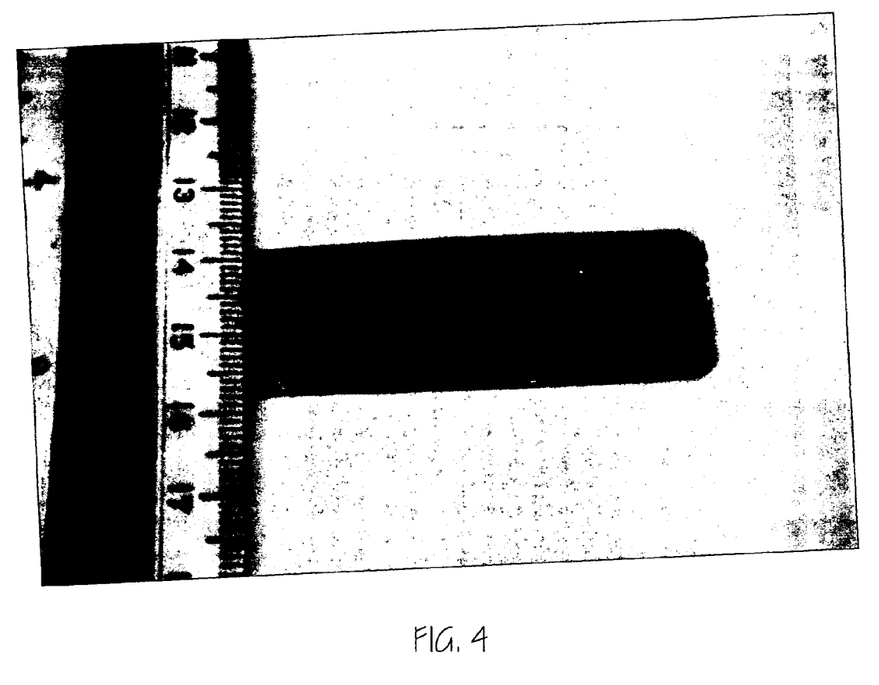
FIG. 4 is a photograph of the adhesive coated surface of the magnetic patch of the current application showing no stripes texture on the face.

FIG. 4 is a photograph of the adhesive coated surface of the magnetic patch tape (1) of the current application showing no stripes texture on the face.

Figure 5:
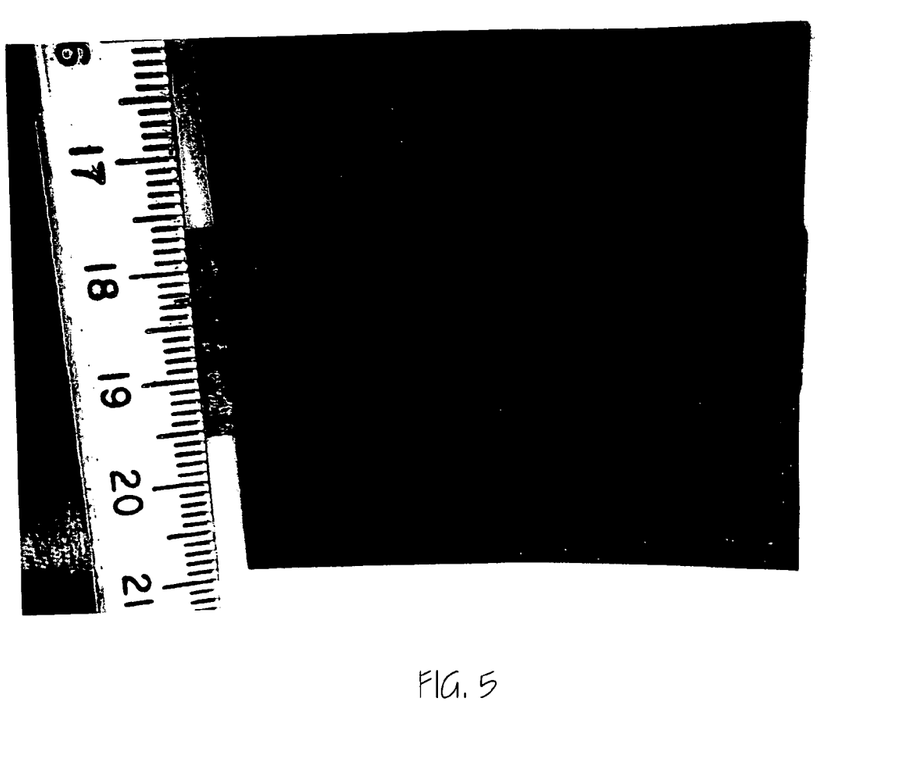
FIG. 5 is a photograph of a magnetic field viewer overlapped on the adhesive coated surface of the magnetic patch of the current application showing stripes of magnetic field.

FIG. 5 is a photograph of a magnetic field viewer overlapped on the adhesive coated surface of the magnetic patch tape (1) of the current application showing stripes of magnetic field. The dark green film is the magnetic field viewer (6) made of two Poly Vinyl Chloride films containing suspending detergent and carbonyl iron powder between the two films. Dimension of the magnetic patch tape is 2 cm by 4.5 cm. 6 dark stripes of 2 mm width are seen along the length of the magnetic patch tape (1) and 6 bright stripes of 1 mm width are seen between the dark stripes.

Figure 6:
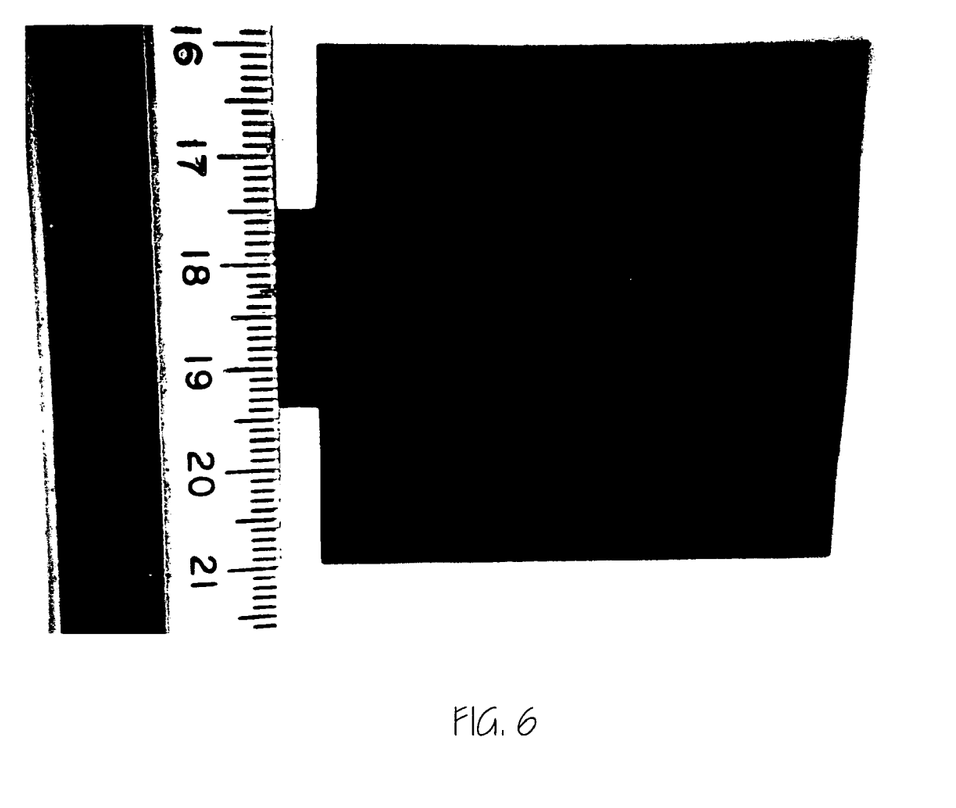
FIG. 6 is a photograph of a magnetic field viewer overlapped on the opposite side of the adhesive coated surface of the magnetic patch of the current application showing no stripes of magnetic field.

FIG. 6 is a photograph of a magnetic field viewer overlapped on the opposite side of the adhesive coated surface of the magnetic patch tape (1) of the current application showing no stripes of magnetic field. This means that the magnetic field is developed not only in a stripe form but also developed to the direction of the second adhesive pasted layer (5), which is attached to a user's skin. Therefore, most of the magnetic field is directed to a user's skin.

Figure 7:
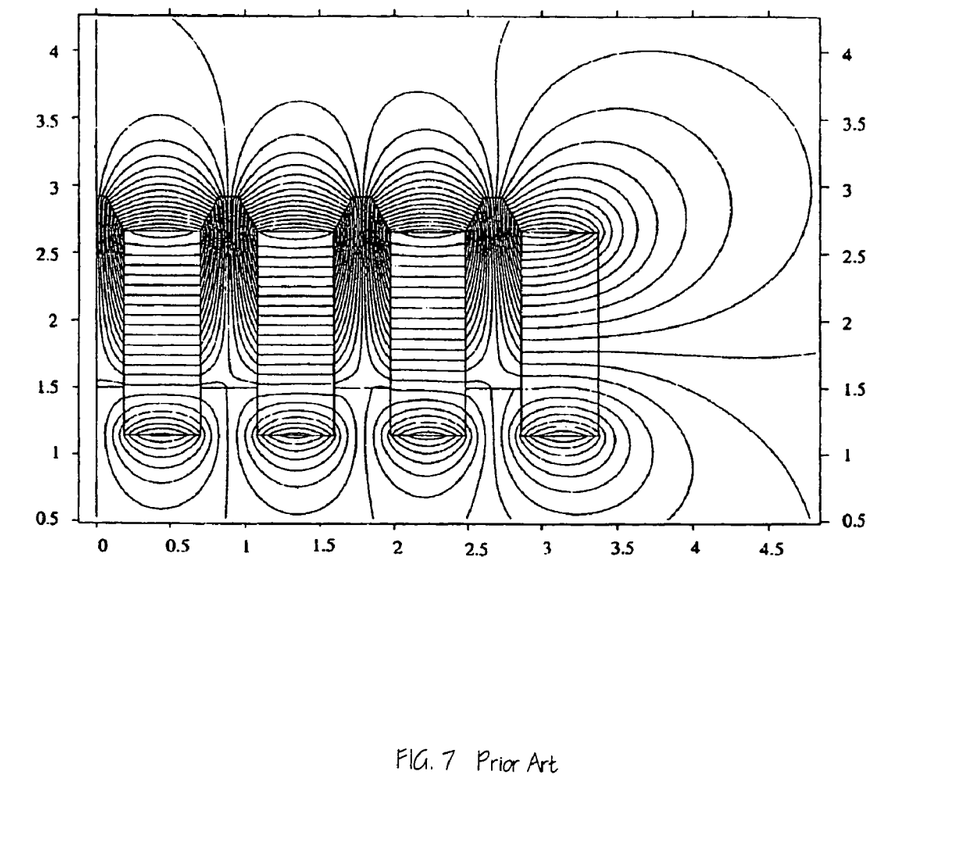
FIG. 7 is a two-dimensional computer modeling of the hybrid magnetic structure of prior art.

FIG. 7 is a two-dimensional computer modeling of the hybrid magnetic structure of prior art, U.S. patent application 20040004523. The hybrid magnetic structure contains blocks of anisotropic magnets aligned in rows between ferromagnetic bars. This shows that the magnetic field is outweighed to the tip of the rod.

Referring to FIGS. 5 to 7, it is possible to conclude that the anisotropic magnetic field of the magnetic patch tape (1) of the current application is designed to outweigh to a user's skin direction.

Figure 8:
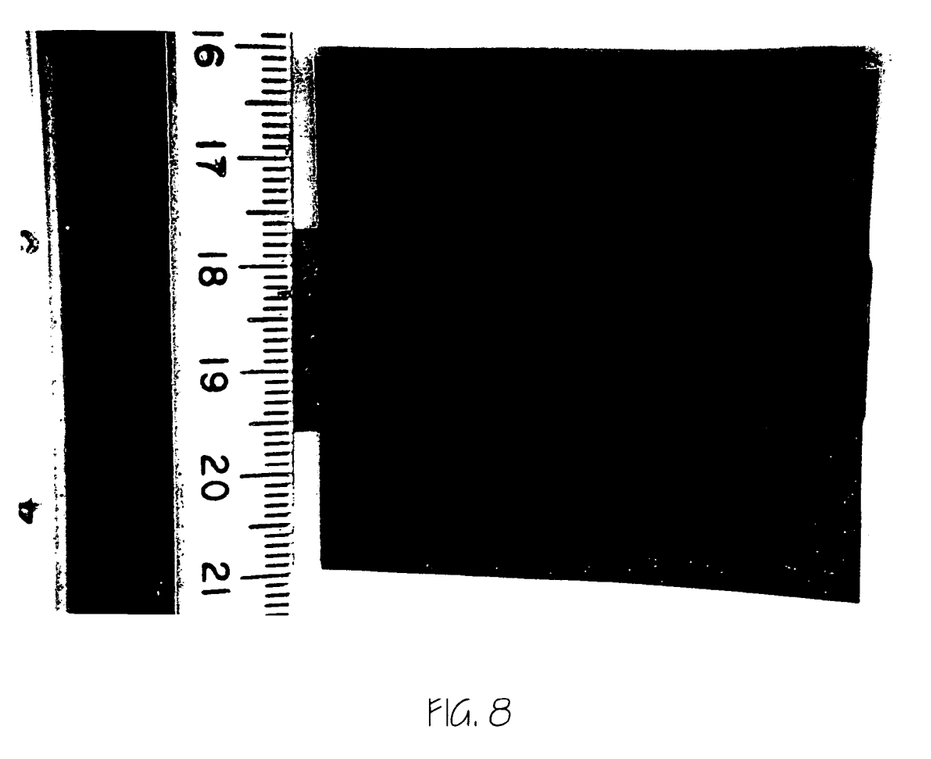
FIG. 8 is a photograph of a magnetic field viewer, where the image of the stripes of magnetic field, which is induced by the magnetic patch tape of the current application, disappears when the viewer is scrubbed against a conventional magnet.

FIG. 8 is a photograph of a magnetic field viewer loosing the image of the stripes of magnetic field, which was induced by the magnetic patch tape of the current application, when scrubbed with a conventional magnet. This shows that the stripes in the magnetic field viewer are not a fixed image and easily changed by another magnetic field.

Figure 9:
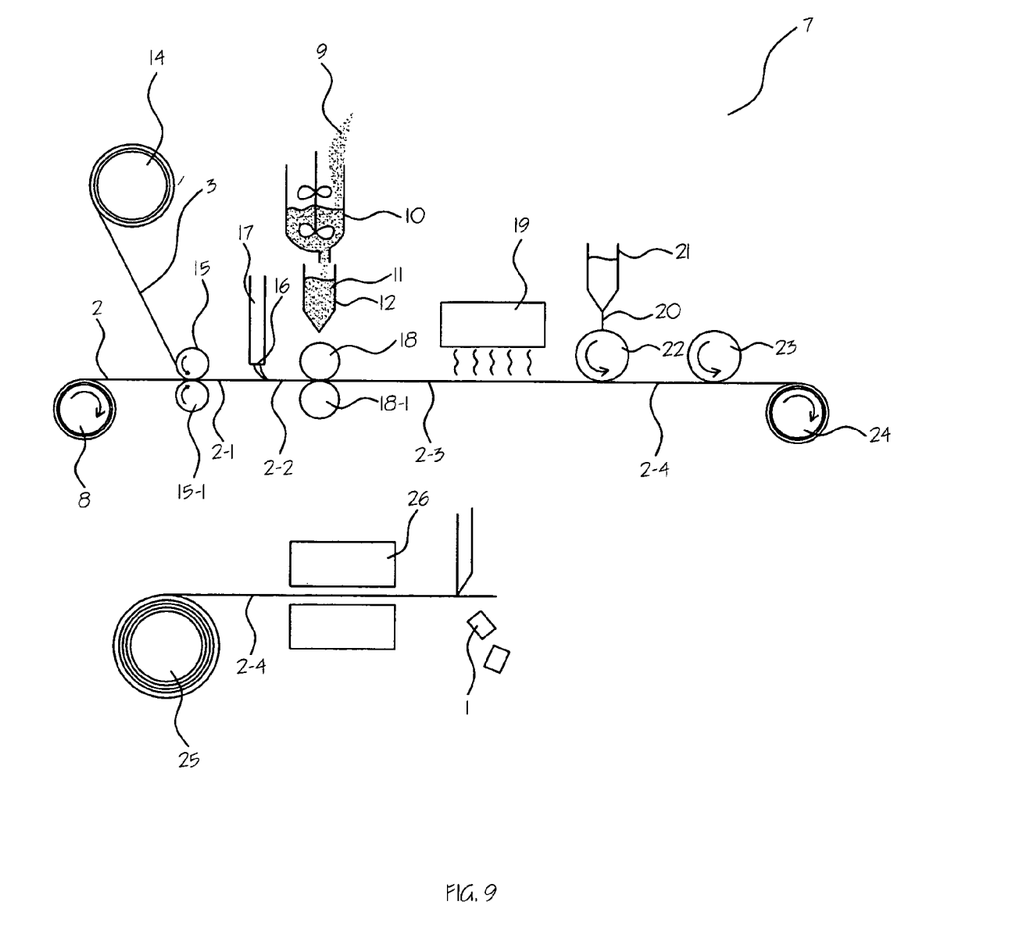
FIG. 9 is a schematic drawing of the process for manufacturing anisotropic magnetic field maintaining patch tape of the current application.
Figure 10:
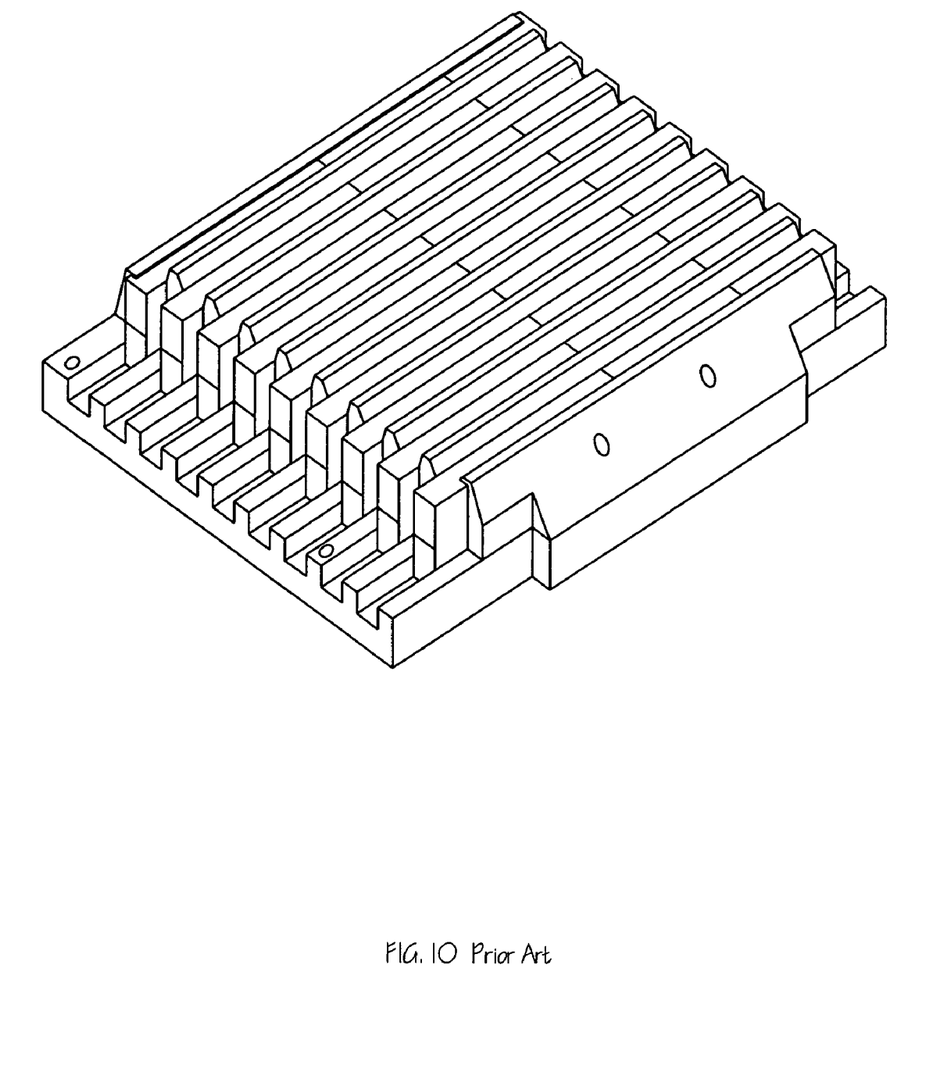
FIG. 10 is a perspective view of the hybrid magnetic structure of the prior art.

FIG. 9 is a schematic drawing of the process for manufacturing the anisotropic magnetic field maintaining patch tape (1) of the current application.

Roll of basic texture (2) is fed to the process line (7) from a un-winder (8). Meanwhile, anisotropic micro-magnet powders (9) of particle size smaller than 1 μm are slurrifyed in a mixer (10) with slurring medium, Vertrel XF from DuPont. Volume ratio of the micro-particle (9) and the Vertrel is in the range of 10 to 50. The prepared slurry (11) is fed to a feeding hopper (12). At the same time, a coating film of LDPE (3) is un-winded from LDPE un-winder (14) and fed to a coating roller (15) equipped with a heater (15-1) to form a composite film (2-1) of LDPE/basic texture. The basic texture (2) is coated with LDPE (3) via the coating roller (15) and the heater (15-1).

First adhesive of Epoxy monomers (16) from a feeder (17) are pasted on the composite film (2-1) of LDPE/basic texture to form a composite film (2-2) of Epoxy/LDPE/Basic Texture.

The slurry (11) of the anisotropic micro-magnet powder (9) is pasted on the composite film (2-2) of Epoxy/LDPE/Basic Texture via feeding rollers (18) and (18-1).

Now, a new composite film (2-3) of anisotropic micro-magnet powder/Epoxy/LDPE/Basic Texture is exposed to a heater (19) to evaporate the slurrifying medium, Vertrel XF from DuPont.

A second adhesive of polyols (20) from a polyol tank (21) are pasted on the composite film (2-3) of anisotropic micro-magnet powder/Epoxy/LDPE/Basic Texture via an adhesive roller (22).

At this moment, another composite film (2-4) of polyol/anisotropic micro-magnet powder/Epoxy/LDPE/Basic Texture is formed. Surface of the last composite film (2-4) is smoothened by a ridge roller (23). And the last composite film is draw-downed and winded by a draw-down roller (24).

The last composite film (2-4) has anisotropic magnetic field that comes from the anisotropic micro-magnet powder (9). But that magnetic field is not strong enough for the application of facilitating blood circulation in a restricted area of a user's skin.

The roll of the last composite film (2-4) is engaged to another un-winder (25) and fed to a magnetizer (26). The inside structure of the magnetizer is similar to that of the prior art of application publication 20040004523. The anisotropic magnet blades have thickness of 3 to 5 mm and were spaced 1 to 3 mm. The applied field strength was 10,000 Gauss.

After that the composite film (2-4) maintains enhanced magnetic field and is cut into desired shape and sizes to be an anisotropic magnet field maintaining patch tape (1).

What is claimed is:

1. A process for manufacturing a magnet patch tape, which shows a number of stripes of anisotropic magnet field with 2 to 5 mm width and spaced 1 to 3 mm apart from each other when viewed through a magnetic field viewer, for facilitating blood circulation of a human body in a restricted area is comprised of:

prepare a slurry of anisotropic magnetic powder having average particle size of less than 1 μm with a surfactant, and coat a roll of plastic structural layer with protecting layer of LDPE via coating rollers to form a composite film of LDPE/structural layer, and paste a first adhesive of epoxy monomers to the composite film of LDPE/structural layer to form a composite film of epoxy monomer/LDPE/structural layer, and paste slurry of anisotropic magnetic powder on the proceeding composite film of epoxy monomers/LDPE/structural layer via a roller to form a composite film of anisotropic magnet powder/epoxy monomers/LDPE/structural layer, and evaporate the surfactant, and coat the composite film of anisotropic magnet powder/epoxy monomers/LDPE/structural layer with a second adhesives of polyols, and smoothen the surface of the second adhesives by passing through a ridge roller to form a patch tape, and stretch the patch tape with a draw down winder, and expose the patch tape to a magnetizer of 10,000 Gauss and having inside structure of anisotropic magnet blades of thickness of 3 to 5 mm spaced 1 to 3 mm to develop anisotropic magnetic field stripes thereon and to form anisotropic magnet field maintaining patch tape, and cut the anisotropic magnet field maintaining patch tape into a desired size.

* * * * *